United States Patent
Kogoi et al.

(10) Patent No.: US 7,186,393 B2
(45) Date of Patent: Mar. 6, 2007

(54) COMPLEX OXIDE, AND PRODUCTION PROCESS THEREFOR AND APPLICATIONS THEREOF

(75) Inventors: Hisao Kogoi, Toyama (JP); Jun Tanaka, Toyama (JP); Hiroyuki Hagihara, Nagoya (JP)

(73) Assignee: Showa Denko K.K., Tokyo (JP)

( * ) Notice: Subject to any disclaimer, the term of this patent is extended or adjusted under 35 U.S.C. 154(b) by 521 days.

(21) Appl. No.: 10/717,483

(22) Filed: Nov. 21, 2003

(65) Prior Publication Data

US 2004/0170551 A1    Sep. 2, 2004

Related U.S. Application Data

(63) Continuation-in-part of application No. PCT/JP02/05054, filed on May 24, 2002.

(60) Provisional application No. 60/293,995, filed on May 30, 2001.

(30) Foreign Application Priority Data

May 24, 2001    (JP)    ............................ P2001-155391

(51) Int. Cl.
    *C01G 9/02*    (2006.01)

(52) U.S. Cl. ................... 423/326; 423/594.14; 424/59; 106/419; 106/426; 106/431; 524/492

(58) Field of Classification Search ................ 423/326, 423/594.14, 622, 623; 424/59, 401, 489; 106/419, 426, 431; 524/492
    See application file for complete search history.

(56) References Cited

U.S. PATENT DOCUMENTS 4,207,377 A * 6/1980 Kindrick ..................... 428/404
6,132,743 A * 10/2000 Kuroda et al. .............. 424/401
6,335,002 B1 * 1/2002 Kogoi et al. .................. 424/63

* cited by examiner

*Primary Examiner*—David Sample
(74) *Attorney, Agent, or Firm*—Sughrue Mion, PLLC

(57) ABSTRACT

The present invention relates to a complex oxide having a BET specific surface area of about 10 to about 200 m²/g, comprising zinc oxide as a primary component, containing crystalline structures of both zinc oxide and silica, and exhibiting diffraction peaks in lattice planes (100), (002), and (101), which are X-ray crystallographically specific to diffraction peaks of crystalline zinc oxide, and in a lattice plane (101) which is X-ray crystallographically specific to the diffraction peak of crystalline silica.

31 Claims, 3 Drawing Sheets

COMPLEX OXIDE, AND PRODUCTION PROCESS THEREFOR AND APPLICATIONS THEREOF

CROSS-REFERENCE TO RELATED APPLICATIONS

This patent application is a Continuation-In-Part of PCT International Patent Application No. PCT/JP02/05054 filed May 24, 2002, which is an application claiming benefit of priority of the filing date of Japanese Patent Application No. 2001-155391 filed on May 24, 2001, and the filing date of U.S. Provisional Application No. 60/293,995 filed on May 30, 2001, pursuant to 35 U.S.C. § 111(b).

BACKGROUND OF THE INVENTION

1. Field of the Invention

The present invention relates to complex oxide particles predominantly containing zinc oxide, whose primary particles exhibit a low degree of aggregation, and which are easily dispersed suspended, or kneaded, with involvement of no pulverization or slight pulverization, in non-aqueous solvents, aqueous solvents, or organic polymer compositions such as resin; to a process for producing the particles; and to applications of the particles.

2. Description of the Related Art

Zinc oxide, also called zinc flower, has long been known as a white pigment. Zinc oxide, zinc oxide doped with a different element, and zinc oxide which has undergone surface treatment such as coating (hereinafter these types of zinc oxide may be collectively referred to as "zinc oxides") exhibit the following optical properties when such zinc oxide is formed into fine particles having a diameter approximately half the wavelength of visible light, the scattering effect of the zinc dioxide particles is reduced considerably. As a result, the particles allow visible light to pass therethrough, and selectively absorb ultraviolet rays by virtue of excellent ultraviolet absorbing effect of zinc oxide.

Conventionally known ultraviolet absorbers include organic ultraviolet absorbers such as benzophenone-based absorbers, benzotriazole-based absorbers, salicylate-based absorbers, and substituted-acrylonitrile-based absorbers. However, a limitation is imposed on incorporation of such an ultraviolet absorber into cosmetics or pharmaceutical products, from the viewpoint of safety. Meanwhile, when such an ultraviolet absorber is incorporated into a thermoplastic resin or a similar material and the resultant mixture is subjected to molding, since the absorber exhibits poor heat resistance, the absorber is decomposed or undergoes bleed-out during molding.

Therefore, zinc oxide exhibiting excellent safety and high heat resistance has become of interest as an ultraviolet absorber. Such zinc oxide is incorporated into cosmetics or pharmaceutical products, or is employed as a filler in, for example, resin films or organic polymer compositions.

Most cosmetics contain organic substances such as oil, fat, wax, and an organic ultraviolet shielding agent; inorganic powder such as a coloring pigment or an extender pigment; and zinc oxides capable of shielding ultraviolet rays. Such zinc oxides must exert excellent ultraviolet shielding effect. In addition, the zinc oxides must exhibit excellent transmission of visible light while maintaining transparency, without causing the skin to be unnaturally highlighted. Furthermore, the zinc oxides must provide a good sensation upon use; i.e., smoothness or slidability, and must exhibit excellent dispersibility when incorporated into other materials.

When zinc oxides are employed as a filler in, for example, resin films or organic polymer compositions, particularly in food packaging film, freshness maintaining film, product display film, or agricultural film, transparency of a medium must be maintained.

Zinc oxides satisfying the aforementioned requirements must assume the form of fine particles, and must exhibit good dispersibility in a medium. Numerous techniques for obtaining such zinc oxides have been proposed.

Japanese Patent Publication (kokoku) No. 60-5529 discloses a method for producing zinc oxide fine particles having a size of about 0.2 to 1 μm, in which zinc assuming a gaseous form (hereinafter may be referred to as "zinc vapor") is oxidized and combusted, and then immediately cooled at a cooling rate of at least 480° C./second. At a temperature of 350° C. or higher, large zinc oxide particles are formed, and the specific surface area thereof is reduced. Therefore, cooling is carried out at such a high rate, to thereby prevent formation of large particles. However, when cooling is carried out at a high rate, oxidation of zinc becomes insufficient, and gray zinc oxide is formed. When such gray zinc oxide is employed in cosmetics, etc., sufficient transparency cannot be obtained. Since production of white zinc oxides requires complete oxidation, sufficient oxidation time must be provided. Therefore, a limitation is imposed on the micronization of zinc oxides.

When zinc oxide is irradiated with ultraviolet rays, the zinc oxide exhibits photocatalytic activity; i.e., excited electrons and generated holes cause various oxidation and reduction reactions. Due to the photocatalytic activity, the zinc oxide decomposes an organic substance which is in contact therewith. Therefore, when zinc oxide whose photocatalytic activity is not suppressed is employed in cosmetics, stability of the cosmetic is lowered. Meanwhile, when such zinc oxide is employed in a filler or a film, an organic substance contained therein is impaired, imparting poor weather resistance to the filler or film.

When zinc oxide is employed in cosmetics or resins, the surface activity of the zinc oxide must be reduced through, for example, surface treatment.

With regard to the surface treatment method, Japanese Patent Application Laid-Open (kokai) No. 3-183620, for example, discloses a method in which zinc oxide fine particles are added to a sodium silicate aqueous solution and stirred and the resultant mixture is subjected to pH adjustment, to thereby form an Si oxide on the surface of the zinc oxide. In the method, reaction is allowed to proceed in a liquid phase, and therefore a solid-liquid separation process and a powder drying process are required. Therefore, aggregation of the resultant powder is inevitable, and dispersibility of the powder is lowered. When the mixture is concentrated and employed in the form of slurry without solid-liquid separation, dispersibility of the slurry is improved as compared with that of the powder, but a great limitation is imposed on the degree of freedom in terms of formulation.

Japanese Patent Application Laid-Open (kokai) No. 2001-558821 discloses a method for preventing photocatalytic activity of zinc oxides by coating the oxides with zinc silicate. However, in the method, reaction is allowed to proceed in a liquid phase, and therefore aggregation of the resultant powder of zinc oxides is inevitable.

Japanese Patent Application Laid-Open (kokai) No. 5-319808 discloses a method in which a metal oxide nucleus is formed through heating, gasification, and thermal decomposition of an organo-metallic salt, and then another type of organo-metallic salt is thermally decomposed on the nucleus, to thereby form a coating layer. In the method, a nucleus formation process and a coating layer formation process must be separated. Since conditions for the nucleus formation process are different from those for the coating layer formation process, control of these processes is difficult, and thus productivity is poor, resulting in high production cost.

As similar techniques, Japanese Patent Application Laid-Open (kokai) Nos. 6-144834 and 6-144833 disclose a method for producing electrically conductive zinc oxide. However, since the amount of a dopant is very small, the photocatalytic activity of zinc oxides is not necessarily prevented.

There have been proposed resin additives or cosmetics containing zinc oxide which is not subjected to surface treatment.

For example. Japanese Patent Application Laid-Open (kokai) No. 7-89710 discloses a method for producing a composition containing uniformly dispersed zinc oxide and silicic acid anhydride, in which a mixture of a sodium silicate aqueous solution and zinc oxide is added to a solution mixture of a surfactant and an organic solvent, a calcium chloride aqueous solution is added to the resultant mixture, and the thus-obtained mixture is subjected to pH adjustment. However, the composition produced through the method contains a small amount of zinc oxide, assumes the form of highly aggregated powder, and exhibits poor ultraviolet shielding and poor transmission of visible light transmission.

Japanese Patent Application Laid-Open (kokai) No. 7-118133 discloses a cosmetic composition containing zinc oxide fine particles, which exhibits excellent transparency, ensures long-term make-up quality because of its high compatibility with free fatty acids contained in sebum, and has excellent ultraviolet shielding property. However, since the cosmetic composition contains zinc oxide having surface activity and an organic substance, decomposition of the organic substance is inevitable, and as a result, stability of the cosmetic composition is impaired.

Japanese Patent Application Laid-Open (kokai) No. 7-25614 discloses zinc oxide exhibiting excellent transmission of visible light and excellent ultraviolet shielding. However, the zinc oxide disclosed in this publication is similar to the zinc oxide disclosed in Japanese Patent Application Laid-Open (kokai) No. 7-118133 in terms of insufficient suppression of the photocatalytic activity of zinc oxide.

As described above, although zinc oxide fine particles obtained through conventional techniques have ultraviolet shielding property, the particles are not easily dispersed in a medium, due to their aggregation. In addition, the particles exhibit insufficient transmittance of visible light; i.e., the particles exhibit low transparency.

SUMMARY OF THE INVENTION

The present invention provides particles whose photocatalytic activity is sufficiently reduced, and which exhibit excellent ultraviolet shielding, transmission of visible light transmission, and dispersibility; a composition containing the particles, the composition exhibiting excellent transmission of visible light and ultraviolet shielding; and production processes for the particles and the composition.

In view of the foregoing, the present inventors have performed extensive studies, and have developed complex oxide particles, each particle containing uniformly dispersed microcrystals of crystalline zinc oxide and microcrystals of crystalline silica, and a process for producing the complex oxide particles.

Also, the present inventors have found that, although the complex oxide particles predominantly contain zinc oxide, the particles do not become large at a temperature of at least 350° C., unlike the case of conventional zinc oxide particles. The present inventors have also found that the complex oxide particles exhibit very useful properties; i.e., the complex oxide particles have excellent ultraviolet shielding property, contain isotropic particles and anisotropic particles assuming a tetrapod shape and/or an acicular shape, exhibit excellent dispersibility, exhibit excellent transmission of visible light, and exhibit suppressed photocatalytic activity. The present invention has been accomplished on the basis of these findings.

Accordingly, the present invention provides the following.

(1) A complex oxide having a BET specific surface area of 10 to 200 $m^2/g$ and comprising zinc oxide as a primary component, characterized by containing crystalline structures of zinc oxide and silica, and exhibiting diffraction peaks in lattice planes (100), (002), and (101), which are X-ray crystallographically specific to diffraction peaks of crystalline zinc oxide, and in a lattice plane (101) which is X-ray crystallographically specific to the diffraction peak of crystalline silica.

(2) A complex oxide according to (1), wherein the crystalline structures of zinc oxide and silica are contained in primary particles of the complex oxide.

(3) A complex oxide according to (1) or (2), wherein tetrapod-shaped particles and/or acicular particles account for about 5 to about 95% by count of the primary particles.

(4) A complex oxide according to any one of (1) through (3), wherein, after the complex oxide is allowed to stand at 800° C. for about one hour, the complex oxide has a BET specific surface area at least 70% that of the complex oxide before being allowed to stand under the above conditions.

(5) A process for producing a complex oxide as recited in any one of (1) through (4), which comprises, in a vapor-phase reaction in which zinc assuming a gaseous form is oxidized in the presence of oxygen and steam, feeding into a reactor a Zn raw material gas containing an inert gas and zinc assuming a gaseous form, and an oxidative gas containing oxygen and steam, to thereby allow the zinc to be oxidized in the reactor; and feeding a silicon-containing composition into a reaction zone of the reactor, to thereby allow oxidation to proceed.

(6) A process for producing a complex oxide according to (5), wherein the silicon-containing composition is fed into a zone up to 1 m downstream of a point at which oxidation of the zinc is initiated.

(7) A process for producing a complex oxide according to (5) or (6), wherein the silicon-containing composition contains an organosilane or a silicon halide.

(8) A process for producing a complex oxide according to any one of (5) through (7), wherein the Zn raw material gas contains zinc in an amount of at least about 1 mol % and about 70 mol % or less.

(9) A process for producing a complex oxide according to any one of (5) through (8), wherein the Zn raw material gas is fed into the reactor at about 900 to about 1,800° C.

(10) A process for producing a complex oxide according to any one of (5) through (9), wherein the Zn raw material gas is fed into the reactor at a rate of about 10 to about 250 m/second.

(11) A process for producing a complex oxide according to any one of (5) through (10), wherein the oxidative gas is fed into the reactor at about 900 to about 1,800° C.

(12) A process for producing a complex oxide according to any one of (5) through (11), wherein the oxidative gas is fed into the reactor at a rate of about 10 to about 250 m/second.

(13) A process for producing a complex oxide according to any one of (5) through (12), wherein the silicon-containing composition is fed into the reactor at about 50 to about 1,200° C.

(14) A process for producing a complex oxide according to any one of (5) through (13), wherein the silicon-containing composition is fed into the reactor at a rate about 30% to about 300% the rate at which the Zn raw material gas is fed into the reactor.

(15) A process for producing a complex oxide according to any one of (5) through (14), wherein the amount of oxygen contained in the oxidative gas is about 5 vol % to about 100 vol %, and the total amount of oxygen and steam contained in the oxidative gas is about 5 vol % to about 100 vol %.

(16) A process for producing a complex oxide according to any one of (5) through (15), wherein the oxidative gas is fed into the reactor through a plurality of nozzles.

(17) A process for producing a complex oxide according to any one of (5) through (16), wherein the silicon-containing composition is fed into the reactor through a plurality of nozzles.

(18) A process for producing a complex oxide according to any one of (5) through (17), wherein the Zn raw material gas is fed into the reactor through a plurality of nozzles.

(19) A complex oxide produced through a production process as recited in any one of (5) through (18).

(20) An organic polymer composition comprising a complex oxide as recited in any one of (1) through (4) and (19) in an amount of about 0.01 to about 80 mass % on the basis of the entirety of the composition.

(21) An organic polymer composition according to (20), wherein the organic polymer of the composition is at least one species selected from the group consisting of a synthetic thermoplastic resin, a synthetic thermosetting resin, and a natural resin.

(22) An organic polymer composition according to (20) or (21), which assumes the form of a compound.

(23) An organic polymer composition according to (20) or (21), which assumes the form of a masterbatch.

(24) A molded product formed through molding of an organic polymer composition as recited in any one of (20) through (23).

(25) A powder comprising a complex oxide as recited in any one of (1) through (4) and (19).

(26) A slurry comprising a complex oxide as recited in any one of (1) through (4) and (19).

(27) A coating agent comprising a complex oxide as recited in any one of (1) through (4) and (19).

(28) A coating material comprising a complex oxide as recited in any one of (1) through (4) and (19).

(29) A structure comprising, on its surface, a complex oxide as recited in any one of (1) through (4) and (19).

(30) A cosmetic composition comprising a complex oxide as recited in any one of (1) through (4) and (19).

DESCRIPTION OF REFERENCE NUMERALS

Figure 1:
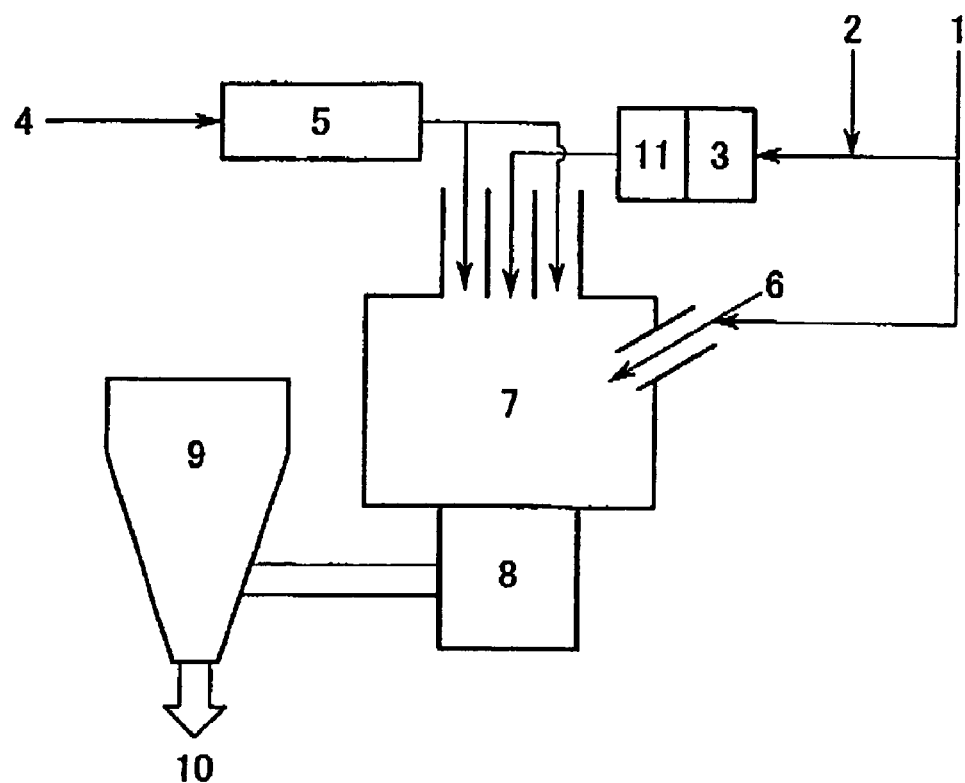
FIG. 1 is a schematic representation showing an exemplary reaction apparatus employed for carrying out the production process of the present invention.

1. Inert gas
2. Metallic zinc
3. Zinc gasification apparatus
4. Oxidative gas
5. Oxidative gas heating apparatus
6. Silicon-containing composition
7. Reactor
8. Cooling apparatus
9. Collecting apparatus
10. Complex oxide
11. Zn raw material gas heating apparatus

DETAILED DESCRIPTION OF THE PREFERRED EMBODIMENTS

The present invention will next be described in detail.

The complex oxide of the present invention can be produced through, for example, the following procedure.

In the case of oxidation reaction of zinc vapor in an atmosphere containing oxygen and steam, an inert gas containing zinc vapor (hereinafter the gas may be referred to as "Zn raw material gas") and a gas containing oxygen and steam (hereinafter the gas may be referred to as "oxidative gas") are fed into a reactor, to thereby oxidize zinc. A silicon-containing composition containing, for example, an organosilane or a silicon halide (hereinafter the composition may be referred to as "Si raw material") is sprayed into the reaction zone in the form of a fluid (preferably in the form of a gas), and the Si raw material is oxidized, to thereby yield the complex oxide of the present invention. The Si raw material may contain an inert gas serving as a carrier gas.

The oxidative gas may be obtained by combusting a combustible gas such as propane or hydrogen by use of excess combustion-supporting gas such as oxygen or air. The oxidative gas, the Zn raw material gas, or the Si raw material may be fed into the reactor through a plurality of nozzles.

The thus-obtained complex oxide contains zinc oxide as a primary component, and exhibits excellent transmission of visible light and ultraviolet shielding, suppressed photocatalytic activity, and good dispersibility, in which crystalline silica is uniformly dispersed in crystalline zinc oxide particles. As used herein, the term "primary component" refers to a component which is contained in the largest amount; i.e., in an amount of more than 50 mass %.

The complex oxide exhibits strong diffraction peaks in lattice planes (100), (002), and (101) which are X-ray crystallographically specific to diffraction peaks of crystalline zinc oxide. In addition, the complex oxide exhibits a strong peak in a lattice plane (101) which is X-ray crystallographically specific to diffraction peak of crystalline silica, since silica is formed in the zinc oxide synthesis reaction zone of very high temperature.

Energy dispersive X-ray analysis (EDX) of the complex oxide shows that silica microcrystals are uniformly dispersed in zinc oxide microcrystals.

When a conventional complex oxide is produced, a substance (a first component) serving as a nucleus is synthesized, and subsequently a second component is added to the substance. Therefore, the resultant complex oxide has a core-shell structure in which the first component is covered with the second component, or the complex oxide assumes the form of a powder mixture of particles of the first and second components, the two types of particles being present separately from each other.

There has not yet been known a complex oxide like the complex oxide of the present invention, characterized in that it is in the form of particles, where each particle has a second crystalline component (silica) uniformly dispersed in a first crystalline component (zinc oxide), and that the complex oxide exhibits diffraction peaks in lattice planes that are X-ray crystallographically specific to both silica and zinc oxide.

The complex oxide of the present invention usually consists of primary particles containing tetrapod-shaped particles and acicular particles in an amount of about 5 to about 95% by count and isotropic particles, the particles being observed by use of a transmission electron microscope (TEM). As used herein, the expression "tetrapod-shaped particle" refers to a particle having branches extending in four different directions from a common base.

The ratio by count of the isotropic particles to the acicular/tetrapod-shaped particles may be controlled by regulating the ratio by amount of a silicon-containing composition to zinc, the composition and zinc being subjected to reaction. The greater the amount of the silicon-containing composition, the greater the amount of the isotropic particles. The smaller the amount of the composition, the smaller the amount of the isotropic particles. By means of energy dispersive X-ray analysis (EDX), each of the above particles, regardless of shape, is found to contain an Si component and a Zn component, the Si component being present uniformly in the Zn component.

When powder of the complex oxide of the present invention; i.e., a powder mixture containing isotropic particles and tetrapod-shaped particles and/or acicular particles, is dispersed in, for example, an aqueous solvent, a non-aqueous solvent, or an organic polymer, the powder exhibits more excellent dispersibility as compared with zinc oxide formed solely of isotropic particles, zinc oxide formed of solely tetrapod-shaped particles, or zinc oxide formed solely of acicular particles.

The reason for the above has not yet been elucidated, but is considered to be as follows. When isotropic particles are appropriately mixed with tetrapod-shaped particles or acicular particles, the distance between the particles is appropriately maintained by virtue of steric hindrance effect, and thus the powder mixture is easily dispersed in a medium.

Excellent dispersibility of the complex oxide of the present invention in both an aqueous solvent and a non-aqueous solvent is considered to be attributed to features of both zinc oxide and silica on the surface of particles of the complex oxide.

In the complex oxide particles of the present invention, the surfaces of zinc oxide particles are not completely covered with silica. However, the photocatalytic activity of the complex oxide particles is reduced to a level such that no practical problems arise when the complex oxide particles are applied to an organic composition. The reason for the above is considered to be as follows. Silica portions existing on the surfaces of the particles, i.e., silica portions projecting from the surface thereof interact relatively strongly with the organic composition, and therefore other organic molecules do not approach the surface of zinc oxide.

In the production process for the complex oxide of the present invention, particles exhibiting suppressed photocatalytic activity can be formed in a single step. Therefore, the thus-formed particles do not require a step for suppressing photocatalytic activity, such as a coating step. Thus, the production process for the complex oxide of the present invention is advantageous in terms of production costs.

The aforementioned feature of the complex oxide particles of the present invention is attributed to excellent heat resistance of the particles. In general, fine particles exhibiting excellent dispersibility are not produced, for the reasons described below. In the case of a liquid phase process, fine particles aggregate through repeated collision and coalition, due to high particle density in a particle formation zone. In the case of a vapor-phase process, since fine particles are formed at high temperature, the particles become large.

The complex oxide of the present invention assumes the form of fine particles; i.e., the oxide has a specific surface area of about 10 to about 200 $m^2/g$ as measured by means of a BET single point method. However, after the complex oxide is allowed to stand in an electric furnace at about 800° C. for about one hour; i.e., the oxide is subjected to heat treatment, the complex oxide attains a BET specific surface area at least 70% that of the complex oxide before heat treatment. When zinc oxide having a BET specific surface area similar to the above value is subjected to the above heat treatment, the zinc oxide attains a BET specific surface area 50% or less that of the zinc oxide before heat treatment.

Unlike the case of conventional zinc oxide, the complex oxide particles of the present invention tend not to become large at high temperature. In addition, aggregation of the particles is prevented, since particle density is relatively low in a particle formation zone. Therefore, the complex oxide particles exhibit excellent dispersibility.

The position of a silica component in the complex oxide of the present invention may be varied by adjusting a reactor's entry position for a silicon-containing composition. In other words, by adjusting a position for a supply of an Si raw material in relation to the oxidation reaction initiation point of zinc, the relative positions of the oxidation zones of zinc and a silicon-containing composition can be varied.

When the supply position for the silicon-containing composition is placed more downstream of the oxidation reaction initiation point of zinc, more silica is doped in the vicinity of a surface rather than a core region, therefore, a proportion of silica in the surface can be raised, A supply position for a silicon-containing composition is preferably within a one-meter range downstream of the oxidation reaction initiation position for zinc. When the supply position is further downstream thereof, a distribution of a component in a resultant oxide tends to be heterogeneous.

The form of a silica component present in the complex oxide of the present invention, when an Si raw material is supplied in a gaseous form, may be varied by regulating the flow rates of gasses to be fed into a reactor. For example, when the Si raw material, Zn raw material, and oxidative gas are individually supplied using a parallel flow nozzle, thereby regulating a relative flow rate thereof, the relative positions of the oxidation zones of zinc and a silicon-containing composition are varied.

When the flow rates of the Si raw material, the Zn raw material gas, and the oxidative gas are regulated such that the oxidation zone of the silicon-containing composition is located downstream of the oxidation zone of zinc, a large amount of silica is caused to be present in the vicinity of the surface of the resultant complex oxide particles as compared with in the center of the particles; i.e., the amount of silica present in the surface of the particles can be increased.

The present invention will next be described with reference to a typical production procedure.

Zinc to be fed to a zinc gasification apparatus may assume the form of powder or an acicular particle. An inert gas may be fed to the zinc gasification apparatus together with metallic zinc serving as a raw material. Examples of the inert gas include, but are not limited to, nitrogen, helium, and argon.

The volume of the inert gas fed to the zinc gasification apparatus is preferably determined such that the mol % of zinc contained in a Zn raw material gas falls within a range of about 1 mol % to about 70 mol % inclusive. The zinc concentration affects the size of complex oxide particles. When the zinc concentration is reduced, powder having an overly large specific surface area may be produced, whereas when the zinc concentration is increased, powder having an overly small specific surface area may be produced.

A Zn raw material gas is fed from the zinc gasification apparatus through a Zn raw material gas heating apparatus to a reactor. The Zn raw material gas is fed to the reactor at a temperature of about 900 to about 1,800° C., preferably about 950 to about 1,300° C. The Zn raw material gas is fed to the reactor at a rate of about 10 to about 250 m/second, preferably about 50 to about 150 m/second.

An oxidative gas is fed to the reactor at a temperature of about 900 to about 1,800° C., preferably about 950 to about 1,300° C. The amount of oxygen contained in the oxidative gas is about 5 vol % to about 100 vol % inclusive, preferably about 50 vol % to about 100 vol % inclusive. The total amount of oxygen and steam contained in the oxidative gas is about 5 vol % to about 100 vol % inclusive. The oxidation gas is preferably fed to the reactor at a rate of about 10 to about 250 m/second.

A silicon-containing composition is gasified together with an inert gas serving as a carrier gas, and fed to the reactor. The silicon-containing composition may be a composition containing at least one species selected from the group consisting of silicon halides such as $SiCl_4$, $Si_2Cl_6$, $Si_3Cl_8$, $Si_4Cl_{10}$, $Si_5Cl_{12}$, $Si_{10}Cl_{12}$, $SiBr_4$, $Si_2Br_6$, $Si_3Br_8$, $Si_4Cl_{10}$, $SiI_4$, $Si_2I_6$, $SiCl_2I_2$, $SiClI_3$, $SiBr_3I$, $SiHI_3$, $SiCl_3I$, $SiH_3Br$, $SiH_2Br_2$, $SiHBr_3$, $SiCl_3Br$, $SiCl_2Br_2$, and $SiClBr_3$; organosilanes formed through bonding of Si and an ethoxy group, a methoxy group, a propoxy group, a butoxy group, etc., such as $Si(OCH_3)_4$, $Si(OC_2H_5)_4$, $Si(O-i-C_3H_7)_4$, $Si(O-n-C_3H_7)_4$, $Si(O-i-C_4H_9)_4$, $Si(O-n-C_4H_9)_4$, $Si(O-sec-C_4H_9)_4$, $Si(O-t-C_4H_9)_4$, and mixtures thereof; and organic silicon compounds formed through bonding of the above compounds of a halogen such as Cl, such as $C_2H_5SiHCl_2$ and $C_2H_5SiCl_3$. The Si raw material is preferably a composition containing an organosilane or a silicon halide.

The Si raw material is fed to the reactor at a temperature between about 50° C. and about 1.200° C. inclusive, preferably at a temperature ranging from the boiling point of the silicon-containing composition to the decomposition temperature of the composition. For example, when tetraethoxysilane is employed, the feeding temperature is preferably between about 170° C. and about 400° C. inclusive, within which tetraethoxysilane does not decompose and assumes a gaseous form.

A inert gas is used so that Si raw material can be introduced into the reaction field, during its introduction, in an amount corresponding to the partial pressure of the gas. This makes it possible for the Si raw material to be introduced into the reaction field in an increased amount at or below the boiling point thereof.

The amount of the Si raw material to be fed is determined such that the amount of Si in the resultant complex oxide is preferably at least 5 mass % and less than 50 mass %, more preferably at least 5 mass % and less than 35 mass %, as reduced to silica.

The feeding rate of the Si raw material is a very important factor for determining distribution of silica in the complex oxide particles. In the case where a parallel flow nozzle is employed, when the feeding rate of the Si raw material assuming a gaseous form is regulated to about 30% to about 300%, preferably about 80% to about 150%, the feeding rate of the Zn raw material gas silica can be uniformly dispersed in the complex oxide particles of the present invention.

When the feeding rate of the Si raw material is regulated to more than about 150% the feeding rate of the Zn raw material gas, a large amount of silica can be caused to be present in the vicinity of the surface of the complex oxide particles as compared with in the center of the particles. In the case where a nozzle other than a parallel flow nozzle is employed, when the Si raw material is fed to the downstream side of the reactor such that the reaction zone of the Si raw material is located downstream of the reaction zone of zinc, an effect similar to the above can be obtained.

When the amount of the silicon-containing composition to be fed is reduced, the total amount of tetrapod-shaped particles and acicular particles can be increased. The total amount of tetrapod-shaped particles and acicular particles affects dispersibility of the complex oxide in a medium. Therefore, the total amount is preferably about 5 to about 95% by count, more preferably about 40 to about 90% by count.

When the Zn raw material gas, the oxidative gas, and the Si raw material satisfy the above conditions, even if these materials are fed in parallel, orthogonally, or obliquely, oxidation reaction proceeds efficiently.

Oxidation reaction proceeds in the reactor of high temperature. In order to completely prevent formation of large particles., the residence time of the above materials at high temperature may be regulated by cooling the materials at a specific site.

The thus-produced complex oxide particles are collected by use of, for example, a bag filter.

An embodiment of the production process employing an apparatus including a parallel flow nozzle will next be described.

FIG. 1 is a schematic representation showing an exemplary production apparatus including a parallel flow nozzle.

Metallic zinc 2 is fed to a zinc gasification apparatus 3 by use of a zinc feeding machine. Simultaneously, an inert gas 1 is fed to the zinc gasification apparatus 3. The resultant Zn raw material gas is fed from the zinc gasification apparatus 3 to a Zn raw material gas heating apparatus 11. The zinc gasification apparatus 3 and the Zn raw material gas heating apparatus 11 may be combined or provided separately. The heated Zn raw material gas is fed from the Zn raw material gas heating apparatus 11 to a reactor 7. An oxidative gas 4 is heated in a heating apparatus 5, and fed to the reactor 7.

A silicon-containing composition 6 is heated in an Si raw material heating apparatus, and fed to the reactor 7. In the reactor 7, the Zn raw material gas and the Si raw material are oxidized by the oxidative gas, to thereby produce a complex oxide. The thus-produced complex oxide is fed to a cooling apparatus 8. Particles of the complex oxide are collected by a collecting apparatus 9 such as a bag filter, to thereby yield a complex oxide powder 10.

Like conventional zinc oxide, the complex oxide of the present invention may be employed in resin products, rubber products, paper products, cosmetic compositions, pharmaceutical products, paint, printing ink, ceramic products, electronic parts, etc. Particularly, the complex oxide is preferably employed in products which require low photocatalytic activity and dispersibility in a medium.

The complex oxide particles of the present invention may be added to, for example, an organic polymer to thereby prepare a composition. Examples of the organic polymer include synthetic thermoplastic resin, synthetic thermosetting resin, and natural resin. Specific examples of the organic polymer include polyolefins such as polyethylene, polypropylene, and polystyrene; polyamides such as nylon 6, nylon 66, and aramid; polyesters such as polyethylene terephthalate and unsaturated polyesters; polyvinyl chloride; polyvinylidene chloride; polyethylene oxide; polyethylene glycol; silicon resin; polyvinyl alcohol; vinylacetal resin; polyacetate; ABS resin; epoxy resin; vinyl acetate, resin; cellulose derivatives such as cellulose and rayon; polyurethane; polycarbonate; urea resin; fluorine resin; polyvinylidene fluoride; phenol resin; celluloid; chitin; starch sheet; acrylic resin; melamine resin; and alkyd resin.

The organic polymer composition containing the complex oxide particles of the present invention can be used in the form of, for example, a coating material (coating composition), a compound (e.g., a resin composition containing the particles), or a masterbatch for molded products containing a large amount of the complex oxide particles. The organic polymer composition may contain additives such as an antioxidant, an antistatic agent, and a fatty acid metallic salt.

The amount of the complex oxide particles of the present invention in the organic polymer composition is preferably about 0.01 to about 80 mass %, more preferably about 1 to about 50 mass %, on the basis of the entirety of the composition. When the polymer composition is subjected to molding, a molded product exhibiting ultraviolet shielding is produced. Examples of the molded product include fiber, film, and plastic molded products.

When the complex oxide particles of the present invention are dispersed in water or an organic solvent, and subsequently a binder is arbitrarily added to the resultant mixture, a coating agent can be prepared. No particular limitation is imposed on the binder material, and the binder material may be an organic or inorganic binder.

Examples of the organic binder include polyvinyl alcohol, melamine resin, urethane resin, celluloid, chitin, starch sheet, polyacrylamide, acrylamide, polyesters such as unsaturated polyesters, polyvinyl chloride, polyvinylidene chloride, polyethylene oxide, polyethylene glycol, silicon resin, vinylacetal resin, epoxy resin, vinyl acetate resin, polyurethane, urea resin, fluorine resin, polyvinylidene fluoride, and phenol resin. Examples of the inorganic binder include zirconium compounds such as zirconium oxychloride, zirconium hydroxychloride, zirconium nitrate, zirconium sulfate, zirconium acetate, ammonium zirconium carbonate, and zirconium propionate; silicon compounds such as alkoxy-silane and silicate; and alkoxides of metals such as aluminum and titanium.

Specifically, the amount of the binder contained in the coating agent is preferably about 0.01 to about 20 mass %, more preferably about 1 to about 10 mass %.

When the amount of the binder is about 0.01 mass % or less, adhesion of the coating agent becomes insufficient after coating, whereas when the amount of the binder exceeds about 20 mass %, problems such as thickening of the agent arise, along with economical disadvantages.

The complex oxide of the present invention may be applied to the surface of a structure, and no particular limitation is imposed on the structure to which the complex oxide may be applied. For example, the structure may be formed from an inorganic substance such as metal, concrete, glass, or ceramic; or an organic substance such as paper, plastic, timber, or leather. Alternatively, the structure may be formed from a combination of an inorganic substance and an organic substance. Examples of the structure include building materials, machinery, vehicles, glass products, electric appliances, agricultural materials, electronic apparatus, tools, tableware, bath products, toiletry products, furniture, clothing, cloth products, fibers, leather products, paper products, sporting goods, futon, containers, eyeglasses, signboards, piping, wiring, brackets, sanitary materials, Automobile parts, outdoor goods, stockings, socks, gloves, masks, and the like.

No particular limitation is imposed on the method for applying the complex oxide to the surface of a structure. For example, the aforementioned organic polymer composition or coating agent may be applied directly to a structure, or may be applied onto a structure having a coating film thereon. In addition, another coating film may be formed on the structure coated with the complex oxide.

EXAMPLES

The present invention will next be described by way of Examples, which should not be construed as limiting the invention thereto.

Example 1

Metallic zinc (3.8 kg/hour) and nitrogen gas heated to 900° C. (25 Nm$^3$/hour) (the symbol "N" denoted "under normal conditions"; the same shall apply hereinafter) were fed to a zinc gasification apparatus, to thereby obtain a Zn raw material gas. The resultant Zn raw material gas was heated to 1,000° C. in a Zn raw material gas heating apparatus.

Separately, an oxidative gas containing steam (3 vol %) and oxygen (97 vol %) (25 Nm$^3$/hour) was heated in an oxidative gas heating apparatus. The temperature of the heated gas was 1,030° C. at an inlet of a reactor.

Tetraethoxysilane (700 g/hour) was heated to 300° C. together with nitrogen.

These were fed into a reactor using a nozzle consisting of tubes which are coaxially aligned each other and each of which are exclusively for the Zn raw material gas, oxidative gas, and nitrogen gas containing tetraethoxysilane respectively in this order from inner side to outer side.

The Zn raw material gas was fed at a flow rate of 100 m/second; the oxidative gas was fed at a flow rate of 90 m/second; and the nitrogen gas containing tetraethoxysilane was fed at a flow rate of 40 m/second. After reaction was complete, the resultant powder was collected by use of a bag filter.

The resultant powder assumed a white color. The powder was subjected to measurement of specific surface area through a BET single point method, by use of a Monosorb-type apparatus (product of QUANTACHROME Corporation), and the specific surface area was found to be 42 m$^2$/g. The powder was subjected to analysis by use of a fluorescence X-ray analysis apparatus (X-ray Spectrometer Simultix 10, product of Rigaku), and the powder was found to contain a silica component in an amount of 4 mass %.

Figure 2:
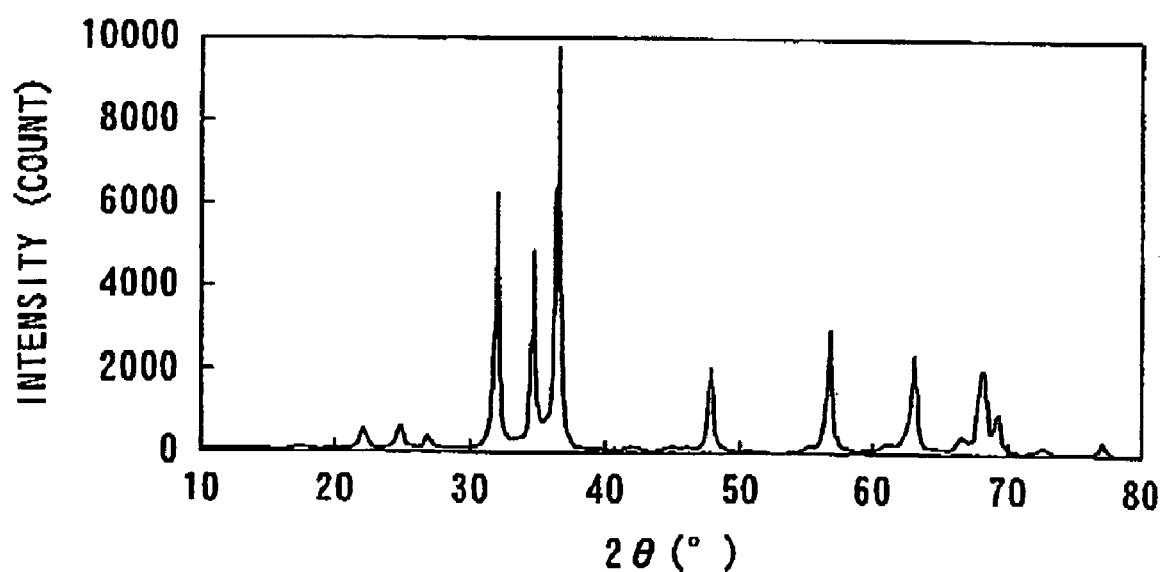
FIG. 2 shows an X-ray diffraction chart of a typical complex oxide of the present invention.

The powder was subjected to analysis of crystal form by use of an X-ray diffraction apparatus (model: 2000/PC, product of Rigaku) under the following conditions: 30 kV, 30 mA, CuKα rays, 2θ=10° to 80°, scanning rate of 2°/min. As a result, the powder was found to exhibit peaks at 2θ=31.8°, 34.5°, and 36.3° corresponding to lattice planes (100), (002), and (101), respectively, the lattice planes being specific to diffraction peaks of crystalline zinc oxide. In addition, the powder was found to have a peak at 2θ=22° corresponding to a lattice plane (101) which is specific to a diffraction peak crystalline silica. The XRD chart of the powder is shown in FIG. 2.

In order to evaluate heat resistance of the powder, a sample was placed in a ceramic crucible, and allowed to stand for one hour in an electric furnace at 800° C. Thereafter, the sample was left to cool to room temperature. The specific surface area of the powder was measured by means of the aforementioned BET single point method. The ratio of the specific surface area after heat treatment to that before heat treatment was found to be 79%.

In order to evaluate the shape of particles, a plurality of transmission electron microscope (TEM) photographs of the powder were taken. On the basis of the resultant photographs, primary particles were classified into anisotropic particles (i.e., tetrapod-shaped particles and acicular particles) and isotropic particles. All the particles (about 300 particles) which had been photographed were counted. As a result, the ratio of tetrapod-shaped particles and a circular particles to all the particles was found to be 83%.

Each of the tetrapod-shaped particles, acicular particles, and isotropic particles was subjected to elementary analysis by means of EDX at a measurement spot size of 5 nm. As a result, each particle was found to contain Zn and Si. A plurality of points of each particle were subjected to the above analysis, and Zn and Si were detected in all the points.

Ultraviolet shielding and transmission of visible light by the powder were evaluated through the following procedure.

Cosmol 43 (product of Nisshin Oil Mills Ltd.) (20 g) and a sample (the complex oxide powder) (200 mg) which had been dried at 105° C. so as to attain constant weight were suspended for 30 minutes at 100 rpm by use of Table Ball Mill V-1M (product of Irie Seisakusho). The resultant suspension was subjected to measurement of percent light transmittance at a wavelength of 280 to 700 mm, by use of UV-VIS spectrophotometer UV-160 (product of Shimadzu Corporation). For measurement, a 0.1-mm quartz cell was employed. Cosmol 43 which had been treated in a manner similar to the above was employed as a blank.

Low light transmittance at 370 nm or less indicates excellent ultraviolet shielding, and high light transmittance at more than 370 nm indicates excellent transmission of visible light; i.e., high transparency.

Figure 3:
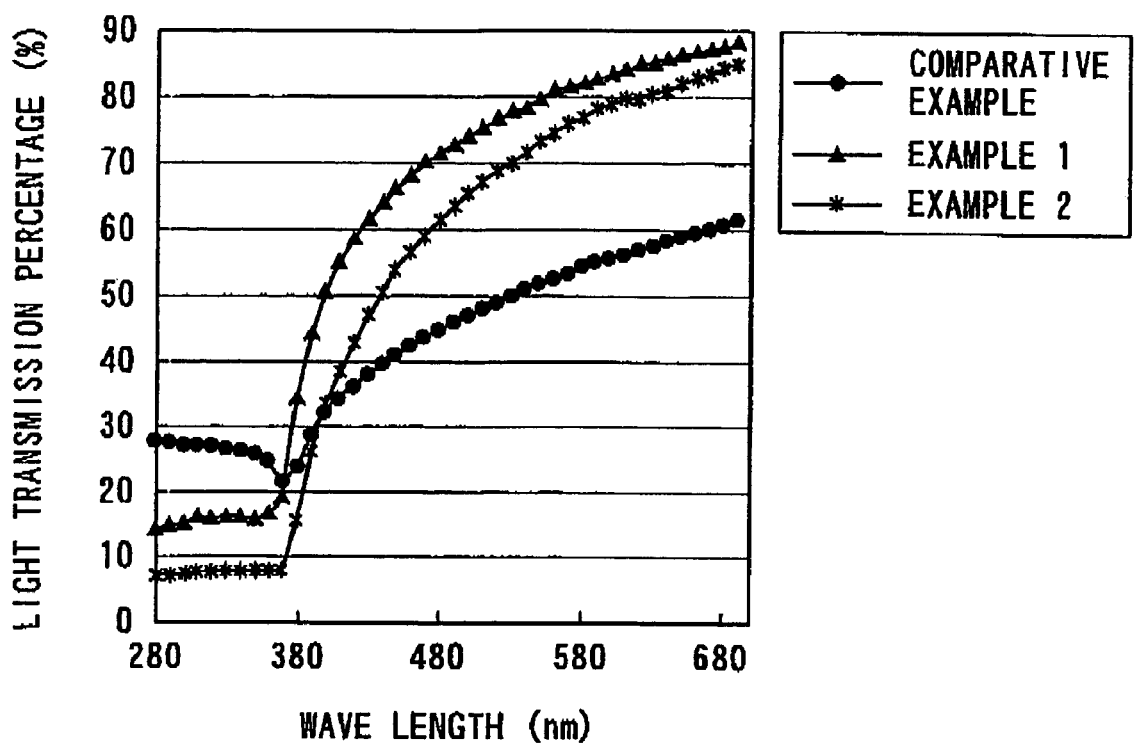
FIG. 3 shows ultraviolet shielding and transmission of visible light transmission of the complex oxide of the present invention and conventional zinc oxide.

The evaluation results are shown in FIG. 3. Light transmittance at less than 420 nm (i.e., ultraviolet region) is low, and light transmittance at 420 nm or more (i.e., visible light region) is high.

Example 2

Metallic zinc (6 kg/hour) and nitrogen gas heated to 900° C. (25 Nm$^3$/hour) were fed to a zinc gasification apparatus, to thereby obtain a Zn raw material gas. The resultant Zn raw material gas was heated to 1,000° C. in a Zn raw material gas heating apparatus.

Separately, an oxidative gas containing steam (3 vol %) and oxygen (97 vol %) (25 Nm$^3$/hour) was heated in an oxidative gas heating apparatus. The temperature of the heated gas was 1.030° C. at an inlet of a reactor.

Tetraethoxysilane (10 kg/hour) was heated to 300° C. together with nitrogen.

These were fed into a reactor using a nozzle consisting of tubes which are coaxially aligned each other and each of which are exclusively for the Zn raw material gas, oxidative gas, and nitrogen gas containing tetraethoxysilane respectively in this order from inner side to outer side.

The Zn raw material gas was fed at a flow rate of 100 m/second; the oxidative gas was fed at a flow rate of 90 m/second; and the nitrogen gas containing tetraethoxysilane was fed at a flow rate of 50 m/second. After reaction was complete, the resultant powder was collected by use of a bag filter.

The resultant white powder was subjected to analysis in a manner similar to that of Example 1.

Figure 4:
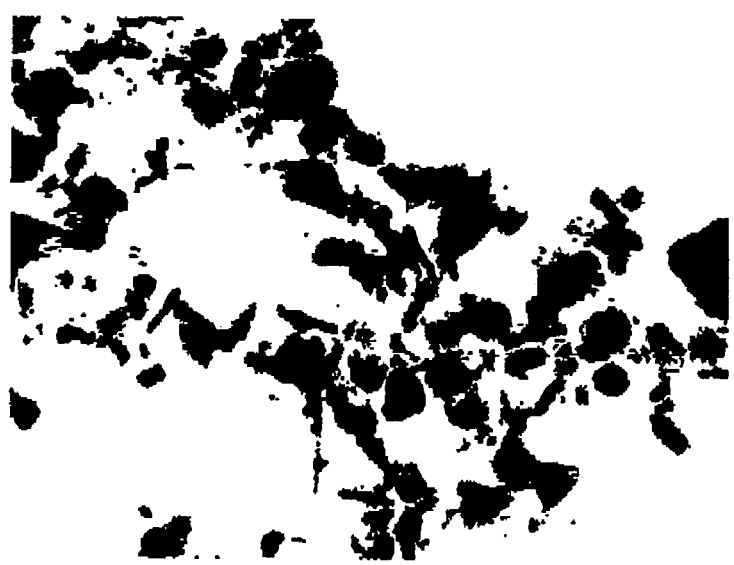
FIG. 4 shows a typical transmission electron microscope photograph of the complex oxide of the present invention.

As a result, the powder was found to have specific surface area of 37 m$^2$/g and to contain a silica component in an amount of 26 mass %. Analysis of crystal form revealed that the powder exhibits peaks at the same 2θ as the powder of Example 1. The ratio of the specific surface area after heat treatment to that before heat treatment was found to be 85%. In order to evaluate the shape of particles, a plurality of transmission electron microscope (TEM) photographs of the powder were taken. An example of the photographs is shown in FIG. 4. The ratio of tetrapod-shaped particles and acicular particles to all the particles was found to be 36%. Each particle was found to contain Zn and Si. Subsequently, the powder was subjected to analysts of ultraviolet shielding and transmission of visible light, and the results are shown in FIG. 3.

Example 3

Pure water was added to the complex oxide powder obtained in Example 1 such that the concentration of the powder became 0.5%, to thereby prepare a slurry. Subsequently, a water-dispersion-type urethane resin (VONDIC1040NS, product of Dainippon Ink and Chemicals, Inc.) was added to the resultant slurry such that the amount of the resin became 70% on the basis of the entirety of the powder, to thereby prepare a coating agent containing the complex oxide and the urethane resin.

Subsequently, a polyester nonwoven fabric (6 deniers, product of Takayasu Co., Ltd.) was impregnated with the above-prepared coating agent, and the resultant fabric was squeezed by use of a roller, followed by drying at 80° C. for two hours, to thereby obtain a polyester nonwoven fabric on which the complex oxide of the present invention was supported.

The above-obtained polyester nonwoven fabric was irradiated with light of 50 mW/cm$^2$ by use of a light fastness tester (SUNSET CPS+, product of ATLAS). One hundred hours after the irradiation, no coloring of the fabric was observed.

Example 4

The coating agent containing the complex oxide powder and urethane resin obtained in Example 3 was applied to one surface of a polyethylene terephthalate film (Lumilar T, product of Toray Industries, Inc.) (thickness: 100 μm), by use of a 25-μm applicator, and then dried at 80° C. for two hours, to thereby form a polyethylene terephthalate film having the complex oxide powder supported thereon.

The thus-formed polyethylene terephthalate film (surface area: 600 cm$^2$) was subjected to weather resistance testing in a manner similar to that of Example 3. As a result, no coloring of the film was observed.

The complex-oxide-particle-bearing polyethylene terephthalate film was subjected to measurement of transmittance by use of a spectrophotometer (UV-2400PC, product of Shimadzu Corporation). As a result, transmittance at 360 nm was found to be 0% and transmittance at 550 nm was found to b 99%.

Example 5

The complex oxide obtained in Example 1 (20 parts by mass), zinc stearate (Zinc Stearate S, product of NOF Corporation) (2 parts by mass), and low-density polyethylene (Jrex JH607C, product of Japan Polyolefins Co., Ltd.) (78 parts by mass) were melt-kneaded at 170° C. (residence time: about three minutes) by use of a twin-screw extruder (model: PCM30, product of Ikegal Iron Works, Ltd.), and the resultant product was pelletized, to thereby produce a low-density polyethylene compound (20 kg) containing the complex oxide in an amount of 20%, each pellet having a diameter of 2 to 3 mmϕ, a length of 3 to 5 mm, and a mass of 0.01 to 0.02 g.

The above-produced low-density polyethylene compound (2 kg) and low-density polyethylene (Jrex JH607C, product of Japan Polyolefins Co., Ltd.) (18 kg) were mixed together for 10 minutes by use of a V-type blender (RKI-40, product of Ikemoto Scientific Technology Co., Ltd.), to thereby prepare a pellet mixture.

Subsequently, the resultant pellet mixture was subjected to extrusion by use of a twin-screw kneading extruder having a T die of 200 mm (KZW15-30MG, product of Technovel Corporation), at a die temperature of 250° C., to thereby form a film having a thickness of 80 μm.

The thus-formed low-density polyethylene film (surface area: 600 cm$^2$) was subjected to weather resistance testing in a manner similar to that of Example 3. As a result, no coloring of the film was observed.

The polyethylene film was subjected to measurement of transmittance in a manner similar to that of Example 4. As a result, transmittance at 360 nm was found to be 0% and transmittance at 550 nm was found to be 90%.

Example 6

A foundation having the below-described formulation was produced through a conventional method. The complex oxide obtained in Example 1 was employed as complex oxide powder.

Formulation of foundation
Complex oxide powder: 30 mass %
Mica: 15 mass %
Talc: 10 mass %
Iron oxide (red): 1.5 mass %
Iron oxide (yellow): 3.5 mass %
Glycerin: 10 mass %
Purified water: 30 mass %
Perfume: appropriate amount The thus-produced foundation exhibited transparency and provided a good sensation upon use.

Comparative Example 1

Metallic zinc (3.8 kg/hour) and nitrogen gas heated to 900° C. (25 Nm$^3$/hour) were fed to a zinc gasification apparatus, to thereby obtain a Zn raw material gas. The resultant Zn raw material gas was heated to 1,000° C. in a Zn raw material gas heating apparatus.

Separately, an oxidative gas containing steam (3 vol %) and oxygen (97 vol %) (25 Nm$^3$/hour) was heated in a heating apparatus. The temperature of the heated gas was 1,030° C. at an inlet of a reactor.

The above-prepared Zn raw material gas and oxidative gas were fed into the reactor through a coaxial twin nozzle. The Zn raw material gas was fed at a flow rate of 100 m/second, and the oxidative gas was fed at a flow rate of 90 m/second. After reaction was complete, the resultant powder was collected by use of a bag filter.

The resultant white powder was subjected to analysis in a manner similar to that of Example 1.

Figure 5:
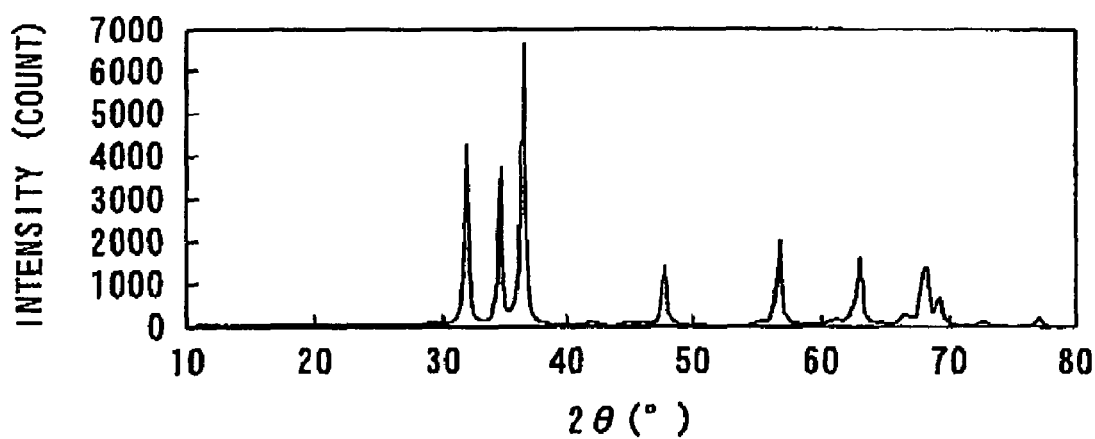
FIG. 5 shows an X-ray diffraction chart of conventional zinc oxide.

As a result, the powder was found to have a specific surface area of 35 m$^2$/g and to exhibit peaks at $2\theta=31.8°$, 34.5°, and 36.3° corresponding to lattice planes (100), (002), and (101), respectively, the lattice planes being specific to the diffraction peaks of crystalline zinc oxide. The X-ray diffraction chart of the powder is shown in FIG. 5. The ratio of the specific surface area after heat treatment to that before heat treatment was found to be 11%. The ratio of isotropic particles to all the particles of the powder was found to be 3%. The results of evaluation of ultraviolet shielding and transmission of visible light are shown in FIG. 3.

Comparative Example 2

The powder obtained in Comparative Example 1 was subjected to weather resistance testing in a manner similar to that of Example 3. As a result, the surface of the powder was found to become turbid, and impairment of a binder was observed.

Comparative Example 3

A foundation was produced in a manner similar to that of Example 6, by use of commercially available zinc flower instead of the complex oxide powder of the invention. Unlike the foundation of Example 6, the resultant foundation exhibited no transparency and provided rough sensation upon use.

INDUSTRIAL APPLICABILITY

The complex oxide of the present invention exhibits excellent transmission of visible light transmission and excellent ultraviolet shielding, and is easily dispersed in a medium. Therefore, the complex oxide is particularly preferably employed in a composition which requires transparency and ultraviolet shielding. Exhibiting suppressed surface activity, the complex oxide of the present invention does not decompose an organic composition which coexists therewith, and thus the complex oxide can be used in an organic composition without surface treatment.

What is claimed is:

1. A complex oxide having a BET specific surface area of about 10 to about 200 m$^2$/g, comprising zinc oxide as a primary component, containing crystalline structures of both zinc oxide and silica, and exhibiting diffraction peaks in lattice planes (100), (002), and (101), which are X-ray crystallographically specific to diffraction peaks of crystalline zinc oxide; and in a lattice plane (101) which is X-ray crystallographically specific to the diffraction peak of crystalline silica.

2. A complex oxide according to claim 1, wherein the crystalline structures of zinc oxide and silica are contained in primary particles of the complex oxide.

3. A complex oxide according to claim 1 or 2, wherein tetrapod-shaped particles and/or acicular particles account for about 5 to about 95% by count of the primary particles.

4. A complex oxide according to claims 1, wherein, after the complex oxide is allowed to stand at about 800° C. for about one hour, the complex oxide has a BET specific surface area at least 70% that of the complex oxide before being allowed to stand under the above conditions.

5. A process for producing a complex oxide as recited in claim 1, which comprises, in a vapor-phase reaction in which zinc assuming a gaseous form is oxidized in the presence of oxygen and steam, feeding into a reactor a Zn raw material gas containing an inert gas and zinc assuming a gaseous form, and an oxidative gas containing oxygen and steam, to thereby allow the zinc to be oxidized in the reactor; and feeding a silicon-containing composition into a reaction zone of the reactor, to thereby allow oxidation to proceed.

6. A process for producing a complex oxide according to claim 5, wherein the silicon-containing composition is fed into a zone up to 1 m downstream of a point at which oxidation of the zinc is initiated.

7. A process for producing a complex oxide according to claim 5 or 6, wherein the silicon-containing composition contains an organosilane or a silicon halide.

8. A process for producing a complex oxide according to claim 5, wherein the Zn raw material gas contains zinc in an amount of at least about 1 mol % and about 70 mol % or less.

9. A process for producing a complex oxide according to claim 5, wherein the Zn raw material gas is fed into the reactor at about 900 to about 1,800° C.

10. A process for producing a complex oxide according to claim 5, wherein the Zn raw material gas is fed into the reactor at a rate of about 10 to about 250 m/second.

11. A process for producing a complex oxide according to claim 5, wherein the oxidative gas is fed into the reactor at about 900 to about 1,800° C.

12. A process for producing a complex oxide according to claim 5, wherein the oxidative gas is fed into the reactor at a rate of about 10 to about 250 m/second.

13. A process for producing a complex oxide according to claim 5, wherein the silicon-containing composition is fed into the reactor at about 50 to about 1,200° C.

14. A process for producing a complex oxide according to claim 5, wherein the silicon-containing composition is fed into the reactor at a rate about 30% to about 300% the rate at which the Zn raw material gas is fed into the reactor.

15. A process for producing a complex oxide according to claim 5, wherein the amount of oxygen contained in the oxidative gas is about 5 vol % to about 100 vol %, and the total amount of oxygen and steam contained in the oxidative gas is about 5 vol % to about 100 vol %.

16. A process for producing a complex oxide according to claim 5, wherein the oxidative gas is fed into the reactor through a plurality of nozzles.

17. A process for producing a complex oxide according to claim 5, wherein the silicon-containing composition is fed into the reactor through a plurality of nozzles.

18. A process for producing a complex oxide according to claim 5, wherein the Zn raw material gas is fed into the reactor through a plurality of nozzles.

19. A complex oxide produced through a production process as recited in any one of claims 5, 6 and 8 to 18.

20. An organic polymer composition comprising a complex oxide as recited in claim 1 in an amount of about 0.01 to about 80 mass % on the basis of the entirety of the composition.

21. An organic polymer composition according to claim 20, wherein the organic polymer of the composition is at least one species selected from the group consisting of a synthetic thermoplastic resin, a synthetic thermosetting resin, and a natural resin.

22. An organic polymer composition according to claim 20 or 21, which assumes the form of a compound.

23. An organic polymer composition according to claim 20 or 21, which assumes the form of a masterbatch.

24. A molded product formed through molding of an organic polymer composition as recited in claim 20.

25. A powder comprising a complex oxide as recited in claim 1.

26. A slurry comprising a complex oxide as recited in claim 1.

27. A coating agent comprising a complex oxide as recited in claim 1.

28. A coating material comprising a complex oxide as recited in claim 1.

29. A structure comprising, on its surface, a complex oxide as recited in claim 1.

30. A cosmetic composition comprising a complex oxide as recited in claim 1.

31. A complex oxide produced through a production process as recited in claim 7.

* * * * *